United States Patent [19]
Levine et al.

[11] Patent Number: 6,004,821
[45] Date of Patent: Dec. 21, 1999

[54] METHOD AND APPARATUS FOR PERFORMING CHEMICAL, QUALITATIVE, QUANTITATIVE, AND SEMI-QUANTITATIVE ANALYSES OF A URINE SAMPLE

[76] Inventors: Robert A. Levine, 31 Pilgrim La., Guilford, Conn. 06437; Stephen C. Wardlaw, 191 N. Cove Rd., Old Saybrook, Conn. 06475

[21] Appl. No.: 09/236,168

[22] Filed: Jan. 25, 1999

Related U.S. Application Data

[60] Provisional application No. 60/077,208, Mar. 7, 1998.

[51] Int. Cl.⁶ .................................................. G01N 33/48
[52] U.S. Cl. ........................... 436/169; 436/63; 436/809; 422/58; 422/61; 422/102; 422/103
[58] Field of Search ................................. 422/56, 58, 61, 422/100–104; 436/63, 169, 808–811

[56] References Cited

U.S. PATENT DOCUMENTS

| | | | |
|---|---|---|---|
| 4,790,640 | 12/1988 | Nason | 350/534 |
| 4,950,455 | 8/1990 | Smith | 422/56 |
| 5,223,219 | 6/1993 | Subramanian et al. | 422/102 |
| 5,427,959 | 6/1995 | Nishimura et al. | 436/534 |
| 5,547,849 | 8/1996 | Baer et al. | 356/244 |
| 5,627,041 | 5/1997 | Shartle | 435/7.24 |
| 5,629,209 | 5/1997 | Braun et al. | 422/100 |
| 5,843,380 | 12/1998 | Staples et al. | 422/102 |

*Primary Examiner*—Lyle A. Alexander
*Attorney, Agent, or Firm*—William W. Jones

[57] ABSTRACT

A urine sample is analyzed for urine chemistry, formed bodies, and rare event evidence, all in a single sample container and under low power magnification. The sample container includes a urine sample receiving chamber which is connected to a urine chemistry chamber, to a formed body isolation chamber, and to a rare events detection chamber, so that the urine can flow from the receiving chamber to the other three chambers. The container may also include a sterile chamber for receiving an auxiliary portion of the urine which may be used for further analysis by the clinician if necessary. The chemistry chamber contains a miniaturized urine dip stick which is scanned by an optical scanning instrument for color emissions. The formed body isolation chamber can be precoated with one or more stains, and is formed with a plurality of different through plane thicknesses whereby smaller formed bodies will be isolated in the smaller thickness regions of the chamber which the larger formed bodies cannot enter. The scanning instrument will scan the isolation chamber and can identify formed bodies by their characteristic light wave emission properties which result from the formed bodies exposure to the stains. The formed bodies can also be morphologically examined in the isolation chamber. The rare event detection chamber will include a component which will absorb essentially all of the water in the urine thus concentrating formed bodies on a surface in the chamber. This chamber can also be provided with one or more stains which will differentially highlight any rare events noted in the chamber by the scanning instrument. Rare events such as casts can be detected in this chamber.

16 Claims, 5 Drawing Sheets

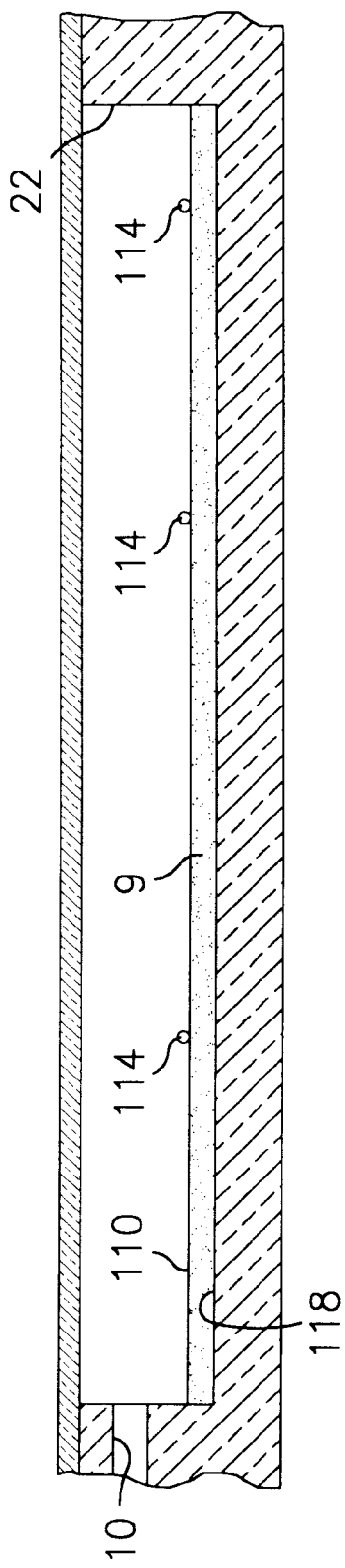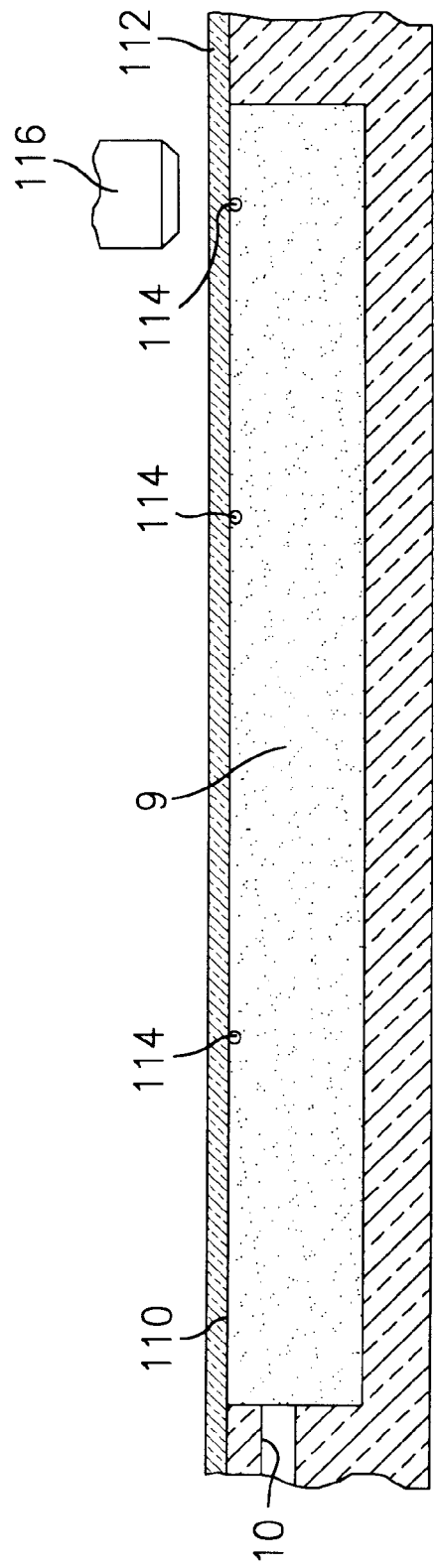

METHOD AND APPARATUS FOR PERFORMING CHEMICAL, QUALITATIVE, QUANTITATIVE, AND SEMI-QUANTITATIVE ANALYSES OF A URINE SAMPLE

This application claims the benefit of U.S. Provisional Application Ser. No. 60/077,208, filed Mar. 7, 1998.

TECHNICAL FIELD

This invention relates to a method and apparatus for analyzing a urine sample. More particularly, this invention relates to a preferably disposable urine sample holder and a method and system for using the same to perform chemical, qualitative, quantitative, and semi-quantitative analyses of a subject's urine sample.

BACKGROUND ART

Urinalysis involves chemical testing of the urine for clinically important chemically detectable constituents and parameters, and examining centrifuged sediment from the urine sample under magnification so as to identify and semi-quantitate the presence of formed bodies in the urine. A general discussion of the present state of the art relating to urinalysis is presented in an article authored by Jonathan Ben-Ezra et al, in *Clinical Chemistry*, Vol 44:1, pages 92–95 (1998).

Chemical testing of a urine sample generally involves analyzing the urine for one or more of the following constituents: glucose; bilirubin; ketones; blood; albumen; nitrites; red blood cells and free hemoglobin; leukocyte esterase; pH; urobilinogin; ascorbic acid; and specific gravity. These various determinations are made through the use of a dipstick having various chemical reagent bands printed thereon. Such dipsticks are commercially available from Bayer Corporation of Elkhart, Ind., as well as other commercial sources. The dipstick is dipped into a well mixed urine sample, and after a time period of thirty seconds to two minutes, the various reagent bands are visually or optically examined for color changes. The bands can be visually compared to a preprinted color chart in order to determine the amount of each of the constituents or parameters being measured. It is also possible to optically scan the dipstick and thereby obtain instrument readings of color intensity or wave length through the use of an instrument manufactured by Ames. Currently available instruments for optically scanning the dipstick bands do not distinguish lysed red blood cells from intact red blood cells, since lysed red blood cells create a different, color distribution on the blood band than do intact red blood cells. With lysed cells, the reaction color is relatively evenly distributed over the blood band, while with whole cells, the reaction color tends to be spotted on the blood band. Presently available instruments do not quantify the number of spots formed on the blood band from whole cells, but can merely quantify the overall color intensity sensed on the band.

In present day technology for quantitatively analyzing a urine sample for the presence of formed bodies such as both red and white blood cells; bacteria; crystals; fecal matter; parasites; spermatozoa; ova from parasites; as well as other formed bodies such as casts, the urine sample is centrifuged so as to separate the liquid phase from the formed body sediment in the urine, thereby concentrating the sediment. Ninety to ninety five percent of the liquid phase is then drawn off from the sediment and discarded, the sediment is re-suspended in the remaining liquid, and a drop of the resuspended sediment is examined under magnification on a microscope slide at low power, i.e., about 100×, for the presence or absence of one or more of the aforesaid formed bodies which are morphologically distinguishable, one from another. This type of analysis provides a crude quantification of target formed bodies which are present in urine.

In present day technology for detecting rare events such as casts in the urine sample, the urine sample sediment is examined as above on a microscope slide. Proteinacious casts which are casts of the renal tubules, may be found in small quantities in normal urine. They may be described by the type of cells they contain such as those having included red cells, which are called red cell casts. The red cell casts are formed in the kidney and are indicative of bleeding in the kidneys prior to the renal collecting ducts and therefore can provide useful information to the clinician. White blood cell casts are indicative of infection of the kidney itself, as opposed to infection in just the urinary bladder. Types of casts include red cell casts, white cell casts, tubular epithelial cell casts, granular or waxy casts containing degenerated cellular components, and clear or hyaline casts. Other than hyaline casts, casts are rarely seen in normal healthy patients, and the range of quantity is described in the literature.

Instruments have been developed which both determine the chemical constituents of the urine and also assist in the microscopic analysis. Such an instrument is the Yellow IRIS, which automatically places the sample on the urine dipstick and then reads the chemical results. For analyzing the particulate components, urine is passed through a flow cell, where a high speed camera captures the images of the particles as they pass through the flow cell and then displays the images so that the technician can classify them. This approach requires less technological time than a purely manual approach, but the instrument is very expensive, prone to malfunctions, and requires a technologist to interpret the particulates which are photographed.

It would be highly desirable to have a single system which could be used to perform a complete urine sample analysis, i.e., urine chemistry, urine blood cell counts, urine bacteria counts, rare event detection, all without significant human intervention, and in an uncomplicated and reliable instrument.

DISCLOSURE OF THE INVENTION

This invention relates to an improved method and paraphernalia for performing a complete analysis of a urine sample. A uniquely configured sample holder is employed for transporting, mixing and dispersing the urine sample, and for providing separate areas in which the various analyses are performed. The sample holder includes a urine sample source well into which the urine sample is introduced and may be transported to the analyzing instrument. The urine sample source well is connected by separate passages with disparate chambers in which the various analyses are performed. A means for re-suspending the urine sediment in the sample prior to introduction into the analytic chambers is included in the sample holder. The sediment re-suspension can be achieved by agitation of the sample holder, or by the inclusion of a mixing ball or balls in the urine sample chamber. One of chambers contains a miniaturized dipstick which is provided with the various reagent bands which allow the complete chemical analysis of the urine sample. A portion of the mixed urine in the source well is drawn off into the dipstick chamber where the urine is absorbed into the dipstick.

A second specially configured chamber which is shallow in one portion and deeper in another portion is provided in the sample holder for analyzing and enumerating the formed bodies, such as blood cells, bacteria and the like, in the urine. The variation of chamber depth is necessary so that the greatest dynamic range of enumeration may be accomplished, as described in co-pending U.S. patent application Ser. No. 09/256,486, filed Feb. 23, 1999. The range of some particulates, such as bacteria, may vary by as much as six logs. This specially configured chamber contains a dry coating of a colorant, such as acridine orange, which is dissolved in the urine and which can differentially highlight the various formed elements, such as blood cells and bacteria which may be present in the urine sample. When stained with a colorant such as acridine orange, it has been observed that the bacteria present in urine may be distinguished from crystalline particulates present in urine by virtue of the bacteria characteristic 540 nm and 620 nm fluorescent emissions when excited by light in the 460 nm range, which is due to the ubiquitous presence of both RNA and DNA in bacteria, and the absence of the same in urate, phosphate, oxalate, and other less frequently seen crystals in urine. The bacteria may be similarly distinguished from cellular particulates, such as leukocytes, epithelial cells, which also contain both RNA and DNA, by the far smaller size of the bacteria. Bacteria in urine range in size from about 0.25 microns to about 3.0 microns, while cells range in size from about 6 microns to about 20 microns in diameter, as well as, with the exception of red cells, possessing a distinct nucleus, which neither crystals nor bacteria possess. Image analysis software incorporated into the scanning instrument facilitates the segmentation of images into bacterial particulates, crystalline particulates, and cellular particulates, and in the manner described in more detail in co-pending U.S. patent application Ser. No. 09/255,673, filed Feb. 23, 1999 is able to quantitate their respective numbers per unit volume of sample, since the volume of each visual field is known.

A third chamber is preferably provided in the sample holder for concentrating a portion of the urine sample so as to enable identification of particles in the urine which could signify the presence of a rare event. The third chamber is connected to the urine source well and includes a water-absorbant layer into which 90–95% of the water content of the urine is absorbed. The third chamber also includes a dry coating of a colorant which is able to differentially highlight any rare event particles which are present in the urine sample. A filter may be included in the third chamber for providing a particle-trapping surface in the third chamber which surface is examined during the analysis.

A sterile chamber may also be provided in the sample holder for the reception and retention of a sterile fraction of the urine sample which is drawn off from the urine source well. The sterile chamber is useful in case the physician desires to perform further bacteriologic analysis of the urine sample by standard microbiologic procedures.

The urine-filled sample holder is placed in an automatic calorimetric scanning instrument which includes an optically magnifying lens set that is focused on the chambers in the sample holder. The instrument includes a CCD component, and is operable to perform an automated X, Y, Z scan of the chambers in the sample holder, and is operative by reason of the CCD to detect and image different colorant wave length emissions emanating from the reagent bands on the dipstick, and from any formed bodies present in the second and third chambers described above. The instrument includes a microprocessor controller which controls the scanning steps and the operation of the CCD imager. The controller is also operative to differentiate the several wave length emissions and correlate the latter with controller pre-programmed emission wavelengths, sizes, shapes, texture and morphology, so as to ascertain the nature of the emission sources, and therefore identify the targets being analyzed. Scanned results can be stored and displayed by means of an on-site display, or can be transmitted to a remote site for analysis. As noted above, a more comprehensive description of the reader instrument and is mode of operation is contained in co-pending U.S. patent application Ser. No. 09/255,673, filed Feb. 23, 1999.

It is therefore an object of this invention to provide an apparatus and method for analyzing a subject's urine sample for chemical analytes, formed bodies, and evidence of a rare event, such as casts, in the patient's urine.

It is a further object of this invention to provide an apparatus and method of the character described which is automated and requires minimal human intervention.

It is yet another object of this invention to provide a disposable urine sample holder for use in conjunction with an apparatus and method of the character described.

It is an additional object of this invention to provide an apparatus and method of the character described which is simple to use and requires minimal technician training.

BRIEF DESCRIPTION OF THE DRAWINGS

These and other objects and advantages of the invention will become more readily apparent from the following detailed description of several embodiments of the invention when taken in conjunction with the accompanying drawings in which:

FIGS. 6 and 7 are sectional views of another embodiment of the invention taken along line 3—3 of FIG. 1;

DETAILED DESCRIPTION OF SPECIFIC EMBODIMENTS OF THE INVENTION

Figure 1:
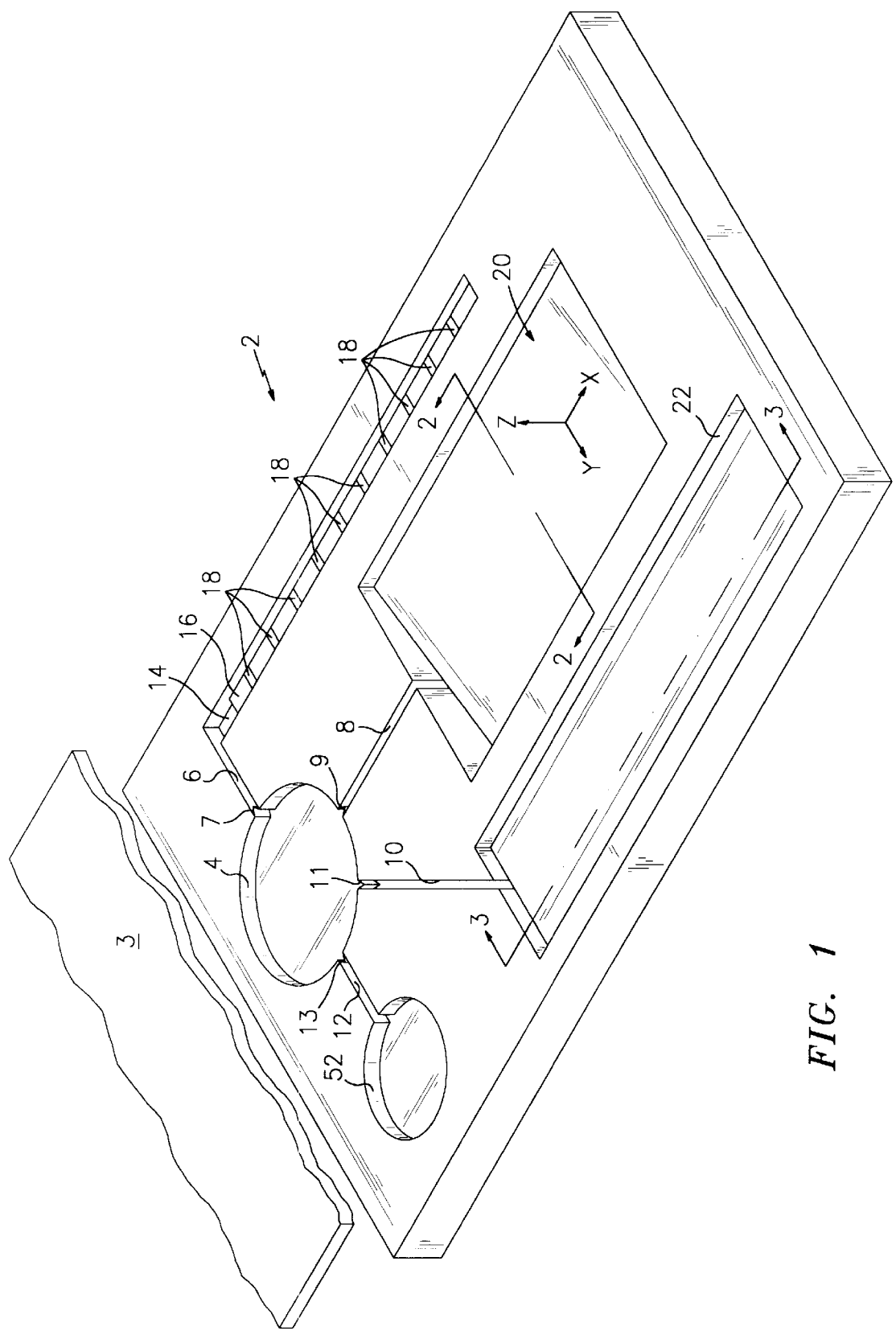
FIG. 1 is a plan view of a urine sample collector formed in accordance with this invention.

Referring now to the drawings, there is shown in FIG. 1 a urine sample container denoted generally by the numeral 2. The sample container 2 preferably has a length which is similar to the length of a conventional microscope slide. The sample container 2 shown in the drawings is rectilinear; however, any shape could be employed that would allow manipulation of the container 2 so as to facilitate scanning of the contents of the several areas of the container 2. The container 2 is provided with a cover 3 which covers the entire top surface of the container 2. The sample container 2 includes a urine sample well 4 into which the urine sample to be analyzed is placed. The well 4 can be sized to contain about two ml of urine, for example. The urine sample well 4 is provided with a plurality of urine flow passages 6, 8, 10 and 12 which lead from the well 4 to various urine receptor chambers in the container 2. The flow passages 6, 8, 10 and 12 are provided with flow control valves 7, 9, 11 and 13, respectively which control the flow of urine from the well 4 through the passages 6, 8, 10 and 12. Urine can be expressed from the well 2 by squeezing the container 2 and cover 3 to open the valves 7, 9, 11 and 13.

One of the chambers 14 is connected to the passage 6 and contains a miniaturized urine chemistry dip stick 16 which includes a plurality of spaced-apart reagent bands 18 which are operative to quantify various constituents in the urine sample. The reagent bands 18 are individually operable to quantify or qualitatively detect various constituents in the urine sample which are indicative of the patient's health. The components of the dip stick 16 are identical to commercially available urine dip sticks, but are miniaturized and fitted into the chamber 14 in the urine sample holder 2.

A second one of the chambers 20 is connected to the passage 8 and is used to detect and quantify formed components which may be found in the urine. Such components include white blood cells, red blood cells, bacteria and crystals. The manner in which the formed component detection is accomplished in the urine sample will be set forth in greater detail hereinafter. Red blood cells will be detected by their absorption of green light due to their hemoglobin content. White blood cells, which are supra-vitally stained by a colorant, such as acridine orange, will be detected by their nuclear fluorescence at 540 nm, and by their cytoplasmic fluorescence at 620 nm. Bacteria will be detected by their fluorescence at the same wavelengths, and will be differentiated from white blood cells by the marked difference in the size of bacteria as compared to the size of white blood cells.

A third one of the chambers 22 is connected to the passage 10 and is used to detect rare events such as casts in the urine sample. The manner in which specific rare events are detected in the chamber 22 will be set forth in greater detail hereinafter.

All of the aforementioned quantification tests are achieved by counting analytes permicroscopic-field and determining analyte concentration in the sample by identifying the volume of each field examined. The volumes of the fields of view are determined by one or more of the methods set forth in co-pending U.S. patent application Ser. No. 09/256,486, filed Feb. 23, 1999.

Figure 2:
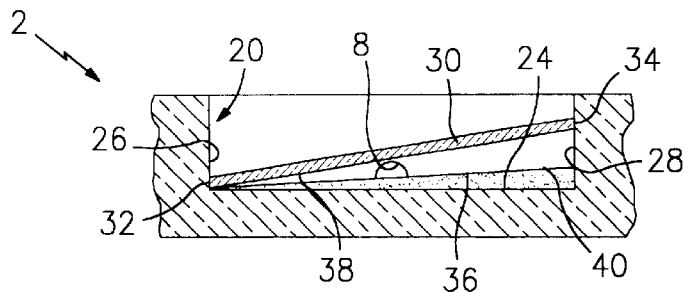
FIG. 2 is a sectional view taken along line 2—2 FIG. 1.

FIG. 2 shows the preferred configuration of the chamber 20. The chamber 20 Includes a bottom wall 24 and side walls 26 and 28. A transparent cover 30 is positioned in the chamber 20 at an angle so that one edge 32 is closely adjacent to or contacts the bottom wall 24 of the chamber 20. The opposite edge 34 of the cover 30 is offset from the bottom wall 24 of the chamber 20. The passage 8 feeds into the chamber 20 below the cover 30 so that urine will be admitted into the chamber 20 below the cover 30 and will disperse throughout the lower section 36 of the chamber 20. It will be noted that the lower section 36 of the chamber 20 is essentially wedge-shaped so that the portion of the urine sample which is positioned in the narrower side 38 of the chamber section 36 will be more thinly spread out than the portion of the urine sample which is positioned in the broader side 40 of the chamber section 36. The result of the thickness of the skewing of chamber section 36 allows the sample to be studied over a dynamic range of sample field thickness or field volumes.

The normal range of white blood cells, red blood cells and casts in patients in various states of health, is described in a text entitled: *A Primer of Urinalysis*; Robert M. Kark et al; Harper and Rowe; (1966). The normal ranges of these components in urine may be exceeded many-fold in illness, so it is necessary to provide an enumerating mechanism which has a wide dynamic range. If the particulate components are too sparsely located, they will be difficult to enumerate, and similarly, if they are too densely located, the analysis algorithms will have difficulty in identifying and enumerating individual cells in such a cell mass. For effective automated analysis, there should be an optimum number of particulates, where they do not overlap. In order to provide an optimum field volume, the analytical chamber must have a varying chamber thickness, or a set of stepped varying chamber thicknesses in order to encompass the expected range of particulate counts, in both health and disease. Thus, a chamber having a varying thickness which varies from about 0.0 to about 3 microns at its thinnest portion, to about 200 microns at its thickest portion so as to allow a 100 fold dynamic range of particulate counts per unit volume of sample.

Figure 3:
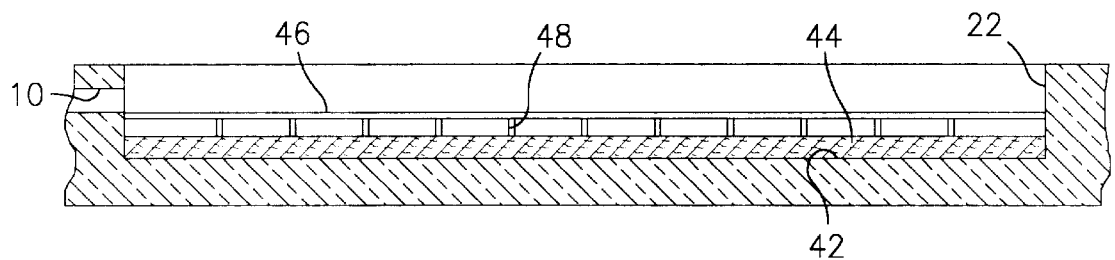
FIGS. 3 and 4 are sectional views of one embodiment of the invention taken along line 3—3 of FIG. 1.
Figure 4:
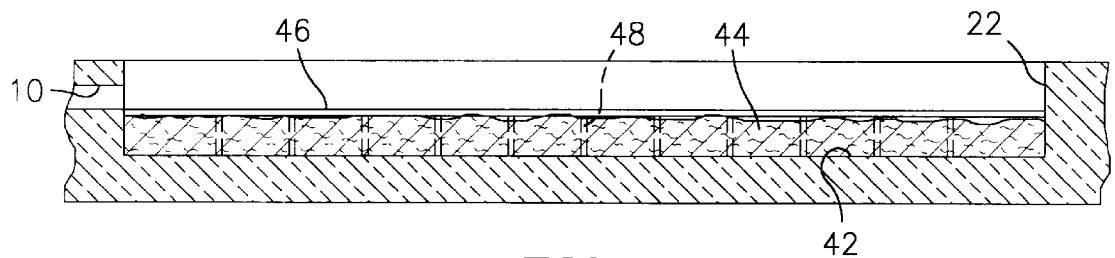
Figure 5:
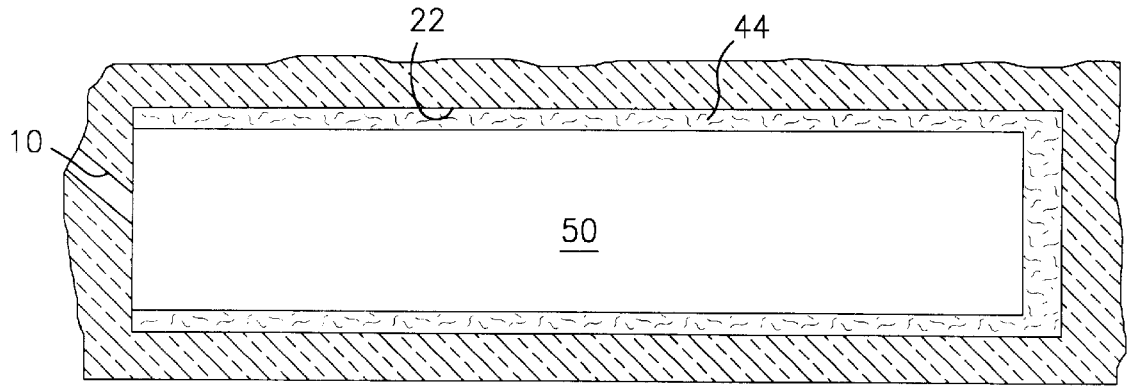
FIG. 5 is a fragmented plan view of a portion of the device of FIG. 1 showing an alternative form of the rare event-detection chamber in the device.

FIGS. 3–5 illustrate details of two embodiments of the structure of the rare event-detection chamber 22. Referring first to the embodiment illustrated in FIGS. 3 and 4, the chamber 22 includes a bottom wall 42 on which a water-absorbant batt 44 is positioned. Above the batt 42 there is positioned a fine pore filter 46, such as a nucleopore membrane filter manufactured by Millipore Corp. The filter 46 is preferably supported by a rigid grid 48 which is mounted in the chamber 22, and through which the water content of the urine can pass. The filter 46 also allows passage of the water content of the urine, but will block passage of formed bodies which are indicative of rare events such as casts. Initially, the water-absorbent batt layer 44 will be spaced apart from the grid 48 and the filter 46, as shown in FIG. 3, since it is dry. As the urine flows into the chamber 22 via the passage 10, the water fraction of the urine sample will pass through the filter 46 and be absorbed in the layer 44 causing the latter to swell as shown in FIG. 4. Formed components in the urine will be trapped on the filter 46 and thus separated from the water in the urine, and because of their placement on the filter 46, they are subject to examination and quantitation by the instrument.

FIG. 5 shows an alternative embodiment of the rare event detection chamber 22. In the alternative embodiment, the absorbent batt 44 is disposed against the side walls of the chamber 22. As the urine flows into the chamber 22 via the passage 10, the water fraction will be wicked off to the sides by the batt layers 44, and any formed bodies in the urine will settle onto the bottom surface 50 of the chamber 22 where they can be detected.

Referring now to FIGS. 6 and 7 there is shown a schematic illustration of another embodiment of the rare event detection chamber 22. The chamber 22 includes a a planar bottom wall 118. A constant thickness layer of a preferably transparent or transluscent dehydrated gel 9 is disposed on the bottom wall 118 of the chamber 22. The top surface 110 of the dehydrated gel layer 9 is planar, mirroring the planar bottom wall 118 of the chamber 22. The volume of the dehydrated gel layer 9 which is disposed in the chamber 22 is such that, when the gel 9 is rehydrated, it will substantially fill the chamber 22. The top of the chamber 22 may be formed by a transparent portion 112, which may take the form of a cover slide, which provides a window through which the top surface 110 of the gel 9 is observed. A plurality of identifiable formed bodies 114 are pre-positioned on the surface 110 and are used to allow the optical instrument 116 to focus on the top surface 110 of the gel 9 after the latter has been rehydrated, as shown in FIG. 7. The formed bodies 114 perform two functions, one being to allow the optical instrument 116 to focus on the gel surface 110; and the other being to confirm the location of the surface 110 when the instrument 116 does not sense any other formed constituents on the surface 110. In the latter case, the instrument 116 will record that the urine sample being analyzed does not contain any significant formed bodies. It will be appreciated that the water constituent of the urine will serve to rehydrate the gel layer 9, and any formed constituents in the urine will be captured on the top surface 110 of the rehydrated gel layer, since they will not be able to penetrate the gel layer 9. Suitable gels include "PHYTAGEL", which is a gel formed from glucuronic acid, rhamnose and glucose. It is clear and colorless, and thus is a good material for use in the detection of formed constituents. This gel is the product of Sigma Diagnostics. Another suitable gel is a transluscent cross-linked sodium polyacrylate gel, which is used in disposable diapers, and the like. It should be noted that the functions of the rare event detection chamber 22 and the quantitation chamber 20 may be combined into a single chamber containing the gel and also having the variable through plane thicknesses. FIG. 2a shows a variation of the chamber 20 which includes the dehydrated gel layer 9 disposed therein.

Referring back to FIG. 1, the sample holder 2 may also include a sterile storage well 52 into which a portion of the urine in the well 4 is drawn through the passage 12. The provision of the sterile storage well 52 allows the physician to have access to a sterile portion of the urine sample in case further testing is indicated from the inspection of any of the chambers 14, 20 or 22. Access may be had to the sterile well 52 to withdraw urine if necessary by means of a sterile syringe, a pipette, or a microbiologic loop.

Figure 8:
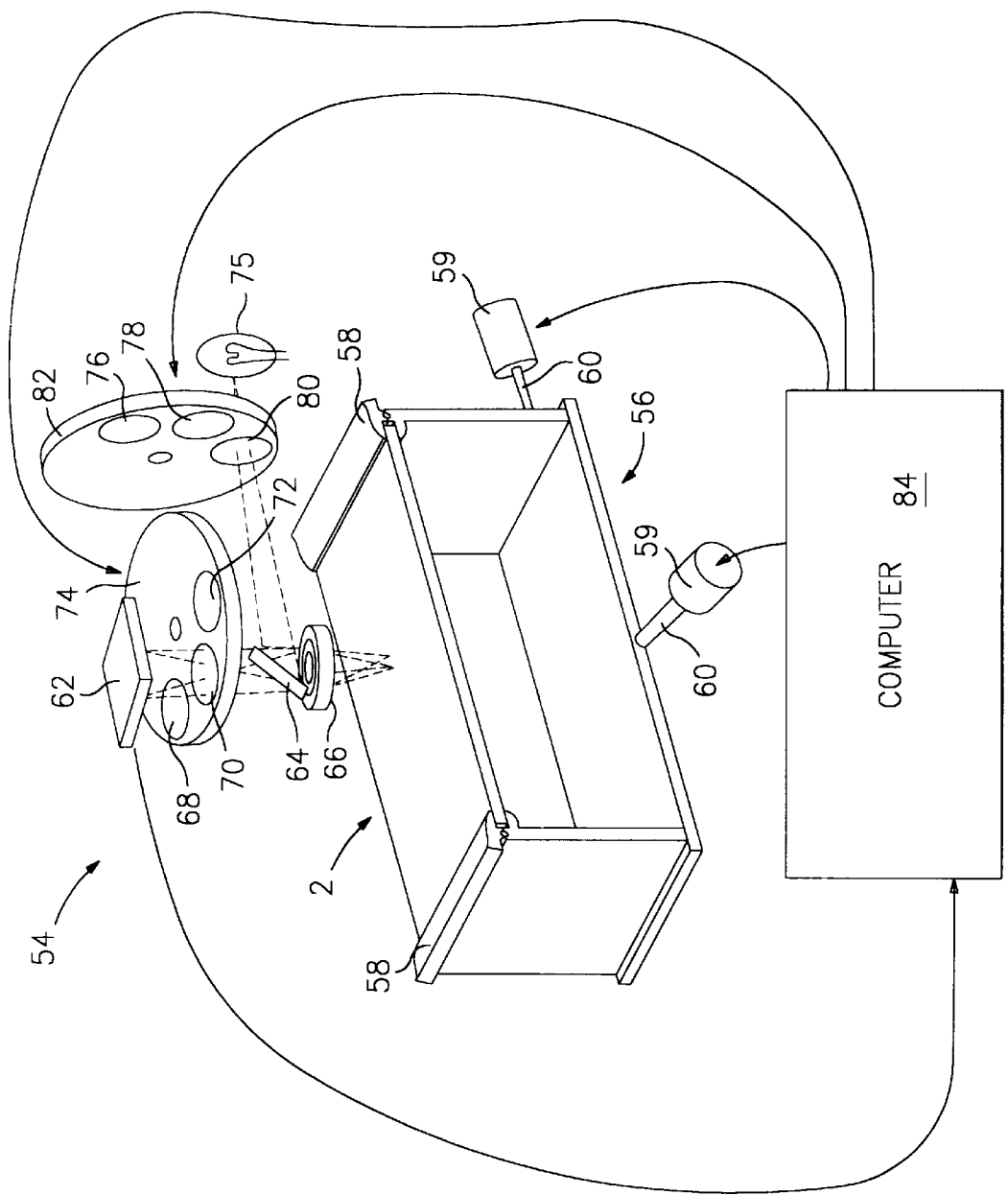
FIG. 8 is a schematic view of an automated microscopical instrument assembly which is adapted for use in conjunction with the urine holder of FIGS. 1–7 so as to perform the complete urine analysis procedure of this invention.

FIG. 8 is a schematic depiction of an automated calorimetric microscopical instrument assembly, which is denoted generally by the numeral 54, and which can be used to scan a urine sample that is contained in the paraphernalia shown in FIG. 1, and can, without significant human intervention, colorometrically analyze the wavelengths of the colors imparted to the dipstick by the urine in the chamber 14; colorometrically and/or morphometrically differentiate between different types of formed bodies, which are specified in part above, in the urine fraction in the chamber 20 being scanned; and can colorometrically and/or morphometrically detect the occurrence of rare events in the urine sample in the chamber 22. The instrument 54 is designed to create and store or transmit the images of the urine sample being scanned. The instrument assembly 54 includes a stage 56 which includes clips 58 which engage the sample holder 2 and enables the sample holder 2 to be moved transversely in the X and Y directions as the contents of the sample holder 2 are scanned.

Reversible electric motors 58 can be used to selectively rotate drive screws 60 in opposite directions so that the sample holder 2 can be transversely moved in the X and Y directions. In this manner, the entire contents of the sample holder 2 can be scanned. The automatic embodiment of the instrument assembly 54 includes a CCD camera 62 which, by means of a beam splitter 64 and lens 66 set, is focused upon the sample-containing portions in the sample holder assembly 2. The CCD camera 62 views and records images of the sample through a plurality of different emission light wave filters 68, 70 and 72 which are mounted on a selectively rotatable filter wheel 74. The instrument assembly 54 also includes an excitation light source 75 which directs an excitation light beam at the sample holder 2 through the beam splitter 64 and the focusing lens set 66. A series of excitation light wave length filters 76, 78 and 80 are mounted on a selectively rotatable filter wheel 82. The excitation light beam is deflected by the beam splitter 64 toward the focusing lens 66, and is focused on the sample holder 2 by the lens 66. Thus, the two filter wheels 74 and 82 allow one to selectively control and vary the wave length of the excitation light source, as well as the emitted light source. A preprogrammed microprocessor controller 84 is operable to selectively control movement of the sample holder 2, the rotation of the filter wheels 74 and 82, and operation of the CCD camera 62. The controller 84 thus enables fully automatic operation of the instrument assembly 12 without the need of significant human intervention.

The manner in which the urine analysis system and method operate is as follows. The chamber 20 in the sample holder 2 will be provided with one or more colorants which will be operable to differentially highlight or label the formed components which may be expected to be found in the chamber 20. The chamber 20, as noted above, is formed with a through plane, or Z axis, thickness that varies from one end of the chamber 20 to the other. The colorant or colorants that can be dry coated onto the surfaces of the chamber 20 can be an intracellular fluorescent dye such as acridine orange, or astrozone orange, or any other colorant capable of highlighting both living and non-living formed components and which will enter target formed components such as white cells, bacteria, and the like, and will differentially label such components, with the exception of crystals. Formed components, such as red cells, which naturally contain pigment will be analyzed using wavelengths appropriate for their pigment. Thus the fluorescent emissions and/or the ratio of light emitted from any formed target components found in the chamber 20, plus any additional morphometric measurements, will be of different wave lengths which are characteristic of the type of formed element. The different target emission wave lengths or morphometric features can be preprogrammed into the controller 84 so that the latter will recognize matching emissions or features that the CCD 62 records and transmits to the controller 84.

For example, the number of red blood cells that are detected in the urine sample per unit volume of the urine sample will indicate whether internal urinary tract bleeding is extant, and, if so, to what extent. The number of white cells that are detected in the urine sample per unit volume can indicate whether the subject is experiencing a urinary tract infection or inflamatory process. The number and types of bacteria detected in the urine sample can be used to diagnose the presence or absence of subject bacterial infections.

Figure 9:
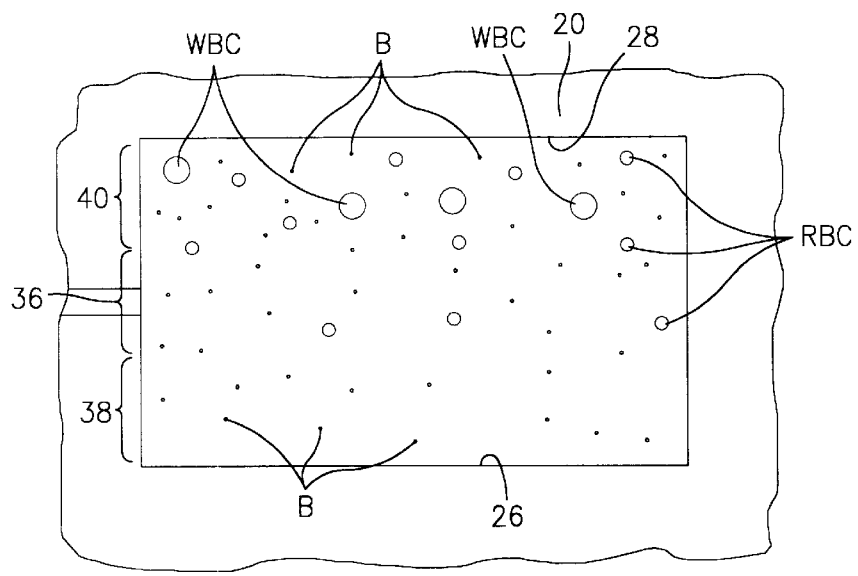
FIG. 9 is a schematic representation of a field of view that could be detected in the formed particle detection chamber in the sample holder.

FIG. 9 illustrates a field of view that could be detected in the formed particle chamber 20. FIG. 9 shows the narrow thickness section 38 of the chamber 20; the intermediate thickness section 36 of the chamber; and the broader thickness section 40 of the chamber 20. As shown in FIG. 9, any bacteria, which are denoted by the letter "B", will be likely to be seen in this section since their concentration, if they are present in the urine sample, is generally high. Red blood cells, which are denoted by the letters "RBC", are best enumerated in the section 36 since red blood cells are relatively intermediate in size, and their concentration is at least 10 fold less than that of bacteria in urine. White blood cells, which are denoted by the letters "WBC", are best enumerated in the section 40 since white blood cells are relatively large in size and their concentration is usually at least 10 fold less than that of bacteria in urine.

As noted above, any bacteria B in the sample will be differentially highlighted in a predetermined manner, and are smaller than other formed bodies in the urine, thus when the instrument scans the section 38, the CCD 62 will detect any bacteria B in the section 38 by light emission and size, and will transmit such information to the controller 84.

Likewise, when the instrument 54 scans the sections 36 and 40, any white cells WBC and red cells RBC in the sections 36 and 40 will be detected by the CCD 62 and the WBC and RBC presence will be transmitted to the controller 84. The instrument scans of the chamber 20 will thus provide an absolute formed body count in the urine sample. Red blood cells are best identified by their light absorbence in either the Soret band at about 415 nm, or the hemoglobin band at about 560 nm. White blood cells are preferably highlighted with a colorant such as acridine orange, and when illuminated with an excitation light of about 460 nm, the nuclei fluoresce at about 540 nm, and the cytoplasmic components fluoresce at about 620 nm. The ratio of these two wavelengths can be used to identify inflammatory cells such as granulocytes, either singly or in clumps, or the presence of other cells such as epithelial cells. In the case of cells other than granulocytes, morphometric features such as the area of the cell cytoplasm and the cell nuclei can be used as identifying features.

Figure 10:
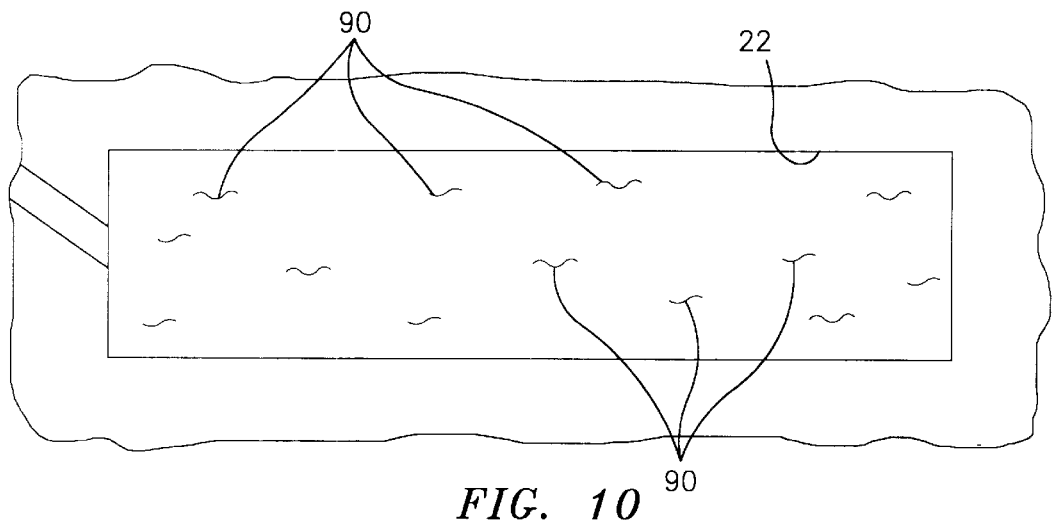
FIG. 10 is a schematic representation of a field of view that could be detected in the rare event detection chamber in the sample holder.

FIG. 10 illustrates the distribution of rare event particles 90 which may be present in the chamber 22. It is noted that the rare events 90, such as casts will be randomly distributed throughout the chamber 22. Identification of any evidence of rare events in the chamber 22 is thus related both to the size of the bodies and the differential coloration of the bodies 90. When the instrument 54 scans the chamber 22, any rare event bodies 90 in the chamber 22 will be detected by the CCD 62 and the rare event body presence will be transmitted to the controller 84. Instrument scans of the chamber 22 will thus provide an absolute rare event body count in the urine sample.

Casts are detected by a combination or their light transmittance, their fluorescence using the wavelengths and colorants described above, and their displacement of colorant within the chamber 22. For example, a cast containing no cellular material, such as a hyaline cast, will not absorb any of the fluorescent colorant, and thus will appear in the chamber as dark characteristic shapes. On the other hand, a cast containing white blood cells will have the characteristic emission of the granulocytes combined with the morphology of a cast. A cast containing red blood cells will have the characteristic light absorption of the red blood cells and the morphology of a cast. Casts containing granular material will have a combination of negative staining in the morphology of a cast and a decrease in light absorbence at all wavelengths due to the presence of the granular material. The container will be provided with some sort of machine-readable indicia, such as a bar code, which the scanning instrument can read and which will tell the scanning instrument where the various chambers are located on the container, and what tests are to be performed in each chamber.

Since many changes and variations of the disclosed embodiments of the invention may be made without departing from the inventive concept, it is not intended to limit the invention otherwise than as required by the appended claims.

What is claimed is:

1. A container for use in performing a plurality of analytical tests on a quiescent urine sample, said container comprising:
   a) a urine sample reception chamber for receiving a supply of urine to be examined;
   b) a urine chemistry chamber containing a urine chemistry dipstick which is operable to detect and quantify various chemical components in a fraction of the urine sample;
   c) a formed constituent isolation chamber which is operable to facilitate the optical detection and optical isolation of various formed constituents which may be present in widely varying concentrations in a fraction of the urine sample from each other so that the isolated formed constituents can be individually examined in the isolation chamber;
   d) a rare event detection chamber which is operable to concentrate rare events in a fraction of the urine sample and separate such rare events from water in the urine, said rare event detection chamber including a water absorbant material which will absorb essentially all of the water constituent of the urine sample fraction which enters the rare event detection chamber and will not absorb any rare events in the urine sample fraction; and
   e) urine fraction transfer passages extending from said urine sample reception chamber to each of said chemistry, isolation and detection chambers.

2. The container of claim 1 wherein said isolation chamber includes at least one colorant which is operable to differentially highlight at least one class of formed bodies which may be found in the urine sample.

3. The container of claim 1 wherein said detection chamber includes at least one colorant which is operable to differentially highlight at least one class of rare event which may be found in the urine sample.

4. The container of claim 1 wherein said isolation chamber includes a smallest through plane thickness region and progressively larger thickness through plane thickness regions.

5. The container of claim 4 wherein said isolation chamber is wedge-shaped.

6. The container of claim 1 wherein said water absorbant material in said detection chamber is a batt which is positioned on a bottom wall of said detection chamber.

7. The container of claim 6 further comprising a formed particle filter which is disposed above said batt, said filter allowing passage of water, but blocking passage of formed particles.

8. The container of claim 1 wherein said water absorbant material in said detection chamber is a batt which is positioned on side walls of said detection chamber.

9. The container of claim 1 wherein said water absorbant material in said detection chamber is a dehydrated gel which is positioned on a bottom wall of said detection chamber.

10. The container of claim 1 further comprising a sterile chamber for receiving a sterile reserve supply of urine from said reception chamber.

11. The container of claim 1 wherein said transfer passages include valves which can be electively opened to allow flow of urine from said reception chamber to the remainder of said chambers in the containers.

12. The container of claim 1 wherein said valves can be electively opened by squeezing said reception chamber.

13. A container for use in performing a plurality of analytical tests on a quiescent urine sample, said container comprising:
   a) a urine sample reception chamber for receiving a supply of urine to be examined;
   b) a urine chemistry chamber containing a urine chemistry dipstick which is operable to detect and quantify various chemical components in a fraction of the urine sample;

c) a formed constituent isolation and rare event detection chamber which is operable to facilitate the optical detection and optical isolation of various formed constituents which may be present in widely varying concentrations in a fraction of the urine sample from each other so that the isolated formed constituents can be individually examined in the isolation chamber and which is operable to concentrate rare events in a fraction of the urine sample and separate such rare events from water in the urine, said rare event isolation and rare event detection chamber including a water absorbant material which will absorb essentially all of the water constituent of the urine sample fraction which enters the isolation and rare event detection chamber and will not absorb any rare events in the urine sample fraction; and d) urine fraction transfer passages extending from said urine sample reception chamber to each of said chemistry, isolation and rare event detection chambers.

14. The container of claim 13 wherein said isolation and rare event detection chamber includes at least one colorant which is operable to differentially highlight at least one class of formed body which may be found in the urine sample, and. at least one colorant which is operable to differentially highlight at least one class of rare event which may be found in the urine sample.

15. A method for performing a plurality of analytical tests on a quiescent urine sample disposed in a container, said method comprising:

a) the step of providing a urine sample reception chamber in said container for receiving a supply of urine to be examined;

b) the step of providing a urine chemistry chamber in said container, said urine chemistry chamber containing a urine chemistry dipstick which is operable to detect and quantify various chemical components in a fraction of the urine sample;

c) the step of providing a formed constituent isolation chamber which is operable to facilitate the optical detection and optical isolation of various formed constituents which may be present in widely varying concentrations in a fraction of the urine sample from each other so that the isolated formed constituents can be individually examined in the isolation chamber; and d) the step of transfering urine from said urine sample reception chamber to each of said chemistry and isolation chambers.

16. A method for performing a plurality of analytical tests on a quiescent urine sample disposed in a container, said method comprising:

a) the step of providing a urine sample reception chamber in said container for receiving a supply of urine to be examined;

b) the step of providing a urine chemistry chamber in said container, said urine chemistry chamber containing a urine chemistry dipstick which is operable to detect and quantify various chemical components in a fraction of the urine sample;

c) the step of providing a formed constituent isolation chamber which is operable to facilitate the optical detection and optical isolation of various formed constituents which may be present in widely varying concentrations in a fraction of the urine sample from each other so that the isolated formed constituents can be individually examined in the isolation chamber;

d) the step of providing a rare event detection chamber which rare event detection chamber is operable to concentrate rare events in a fraction of the urine sample and separate such rare events from water in the urine, said rare event detection chamber including a water absorbant material which will absorb essentially all of the water constituent of the urine sample fraction which enters the rare event detection chamber and will not absorb any rare events in the urine sample fraction; and e) the step of transfering urine from said urine sample reception chamber to each of said chemistry, isolation and detection chambers.

\* \* \* \* \*